United States Patent [19]

Cox et al.

[11] Patent Number: 6,010,687
[45] Date of Patent: Jan. 4, 2000

[54] DEODORANT COMPOSITION

[75] Inventors: Caroline-Ann Margaret Cox, St Helens; Thomas Stirling, Bebington, Wirral, both of United Kingdom

[73] Assignee: Helene Curtis, Inc., Chicago, Ill.

[21] Appl. No.: 09/204,572

[22] Filed: Dec. 3, 1998

[30] Foreign Application Priority Data

Dec. 10, 1997 [GB] United Kingdom .................. 9726132

[51] Int. Cl.⁷ .............................. A61K 7/32; A61K 7/00
[52] U.S. Cl. ............................ 424/65; 424/400; 424/401
[58] Field of Search ................. 424/65, 400, 401

[56] References Cited

U.S. PATENT DOCUMENTS 4,478,821 10/1984 Carrillo .

FOREIGN PATENT DOCUMENTS

| 0174128 | 3/1986 | European Pat. Off. . |
| 1409533 | 8/1975 | United Kingdom . |
| 94/15649 | 7/1994 | WIPO . |

OTHER PUBLICATIONS

International Search Report Application No. PCT/EP 98/07323 completed Mar. 23, 1999.

*Primary Examiner*—Shelley A. Dodson
*Attorney, Agent, or Firm*—Matthew Boxer

[57] ABSTRACT

A deodorant composition for topical application to human skin characterised in that it comprises an effective amount of polyhexamethylene biguanide and an effective amount of chlorhexidine in a cosmetically acceptable carrier.

10 Claims, No Drawings

DEODORANT COMPOSITION

This invention relates to deodorant compositions suitable for application to human skin. In particular, it refers to deodorant compositions comprising polyhexamethylene biguanide (PHMB) or salts thereof and chlorhexidine or salts thereof.

Typically, a deodorising composition will attempt to significantly reduce or prevent body odour by reducing either perspiration or the number of microorganisms on the surface of the skin. The former is usually referred to as an antiperspirant composition and the latter a deodorant.

Compositions reducing perspiration often comprise a metal salt, such as aluminium or zirconium salt which blocks the sweat pores. This method is very simple yet a perspiration reduction of more than 50% is rarely achieved.

Deodorants, on the other hand, reduce the numbers of microorganisms on the surface of the skin. It is well known that sweat is odourless until it has been degraded by the skin microflora. Typical deodorants include ethanol and Triclosan (2',4,4'-trichloro,2-hydroxy-diphenyl ether) which is a well known antimicrobial agent. However, the deodorising effect obtained with such deodorants wears off rather rapidly as the microflora soon recover their numbers.

There is, therefore, a requirement for more effective, longer lasting deodorants on the market.

PHMB is a well-known antimicrobial agent and is commercially available, e.g. from Zeneca under the tradename Cosmocil CQ. The use of PHMB in deodorant compositions is described in U.S. Pat. No. 4,478,821 (Gillette) which discloses the ability of PHMB to reduce body malodour. It teaches in column 2, lines 6 to 15, the poor correlation between antimicrobial activity and deodorant activity. WO 96/31189 (Unilever) also discloses the use of PHMB for use in a propellant driven aerosol deodorant composition. Furthermore, EP B1 0 180 309 (Bausch & Lomb Inc) describes the use of PHMB in disinfecting solutions for contact lenses.

Chlorhexidine is also a well-known antimicrobial agent and is commercially available, e.g. from ICI under the tradename Hibitane.

The use of chlorhexidine or PHMB in combination with the antimicrobial agent hexetidine is disclosed in EP B1 0136 231 (Salkin). This reference describes the use of either chlorhexidine or PHMB in combination with hexetidine (a pyrimidinamine) in disinfectant compositions which are particularly suitable for sterilising surgical instruments. Chlorhexidine or PHMB in combination with an amine oxide is exemplified in DE-A-3334555 (Johnson & Johnson Baby Products Co) as an antimicrobial mixture against gram positive and gram negative bacteria. A combination of chlorhexidine and PHMB is described as a preservative system for opthalmic solutions and particularly for contact lens solutions.

We have now surprisingly found that the combination of PHMB and chlorhexidine in a deodorant composition provides an improved deodorising effect. The two compounds appear to act synergistically and the deodorising effect is greater and longer lasting than would be expected on the basis of the effect of each compound alone.

Both substances are biguanides: chlorhexidine being a bisbiguanide and PHMB being a polymeric biguanide. The structural similarity between the two suggests that they exert their cidal effects in a similar fashion and thus demonstrate at best a cumulative effect and at worst a complementary inhibitory rather than a synergistic effect when used together.

Accordingly, the invention provides a deodorant composition for topical application to human skin comprising in combination polyhexamethylene biguanide and chlorhexidine in a cosmetically acceptable carrier.

All expressions of quantity as a percentage described in this specification relate to percentages by weight unless otherwise stated.

The cosmetically acceptable PHMB for use in compositions according to the invention are represented in the protonated form of the following general formula:

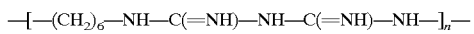

$$-[-(CH_2)_6-NH-C(=NH)-NH-C(=NH)-NH-]_n-$$

wherein n may have a value of up to 500 or more, but typically has a value of 1–40. In preferred embodiments of the invention, n has an average value of 10–14. The polymer is terminated by a suitable end group as described in the references above, such as of formula $-(CH_2)_3-NH-C(NH)-NH-CN$ or $-(CH_2)_3-NH_2$.

The PHMB salt can be present in compositions according to the invention in an amount from 0.001 to 1.0%, more preferably from 0.01 to 0.5% and most preferably from 0.02 to 0.3%.

The chlorhexidine salt can be present in compositions according to the invention in an amount from 0.005 to 0.5%, more preferably from 0.01 to 0.3% and most preferably from 0.01 to 0.2%.

The weight ratio of chlorhexidine: PHMB (expressed as their respective salts) is preferably selected in the range of from 1:2 to 10:1 and especially from 1:1 to 4:1.

Where the composition is intended for use in a metallic canister, as in a conventional pressurised aerosol, the salts of the chlorhexidine and PHMB are preferably halidefree.

Compositions according to the present invention advantageously contain a low molecular weight aliphatic alcohol, preferably containing up to 4 carbons and especially a monohydric alcohol such as ethanol, which can act in combination with the chlorhexidine and PHMB to provide deodorancy on human skin which is superior to that provided by the constituents of the combination alone. The proportion of such an alcohol in the composition is often selected within the range of from 10 to 80% by weight, and in many formulations, from 30 to 70% by weight. The weight ratio of the alcohol, and especially ethanol to the combined weight of PHMB and chlorhexidine salts is preferably selected in the range of from 100:1 to 4000:1, and in many instances from 300:1 to 2000:1.

The composition according to the invention may also comprise other materials commonly found in deodorant or antiperspirant compositions. In practice, the invention composition usually contains at least one cosmetically acceptable vehicle in addition to PHMB and chlorhexidine. The cosmetically acceptable vehicle can comprise a liquid carrier such as an as described hereinbefore, and/or water and/or a hydrophobic carrier which can for example be a volatile or non-volatile silicone oil, or a liquid hydrocarbon or a water-insoluble alcohol or aliphatic ethers or aliphatic or aromatic esters. The carrier normally constitutes from 10 to 80% w/w of the composition.

The invention compositions can additionally contain if desired one or more additional deodorant actives, often from 0 to 5% w/w; perfumes, often from 0 to 2% w/w; antiperspirant actives such as aluminium or zirconium antiperspirant actives, often from 0 to 40% w/w and when present particularly from 5 to 28 % w/w; skin benefit agents, including emollients, which can be provided by a number of carriers such as silicone oils or additionally by for example solid silicone polymers, such additional emollients often comprising from 0 to 20% w/w; colours, often from 0 to 2% w/w; humectants, such as sorbitol or glycerol, often from 0 to 10% w/w; thickeners such as starches or cellulose derivatives, often from 0 to 5% w/w and particularly from 0 to 2% w/w; gellants such as dibenzoyl sorbitol, hydroxystearic acid, stearyl alcohol, or amide derivatives of tricarboxylic acids, often in an amount of from 0 to 15% w/w, and particularly from 0 to 5% w/w; suspension agents, such as clays or silicas, often in an amount of up to 5% w/w; structurants such as silicone elastomers or silicone or hydrocarbon waxes, for example in an amount of 0 to 15% w/w; propellants, such as hydrocarbons having a boiling point of below 10° C., eg butane and propane isomers, such as in an amount, when employed, of from 30 to 95% w/w, particularly 35 to 75% w/w; and other cosmetic adjuncts conventionally employed in such compositions. Where water and a hydrophobic material is present, the composition preferably contains an emulsifier/system, typically having an HLB or averaged HLB of from 6 to 11, such as polyethoxylate ethers or esters. The use of such substances and the proportions in which they are incorporated depend on the form of the composition which may be an aerosol, stick, roll-on, gel, lotion, cream, ointment, powder, suspension or soap.

The invention will now be described by the following non-limiting example.

EXAMPLE 1

Formulations A, B and C summarised in Table 1 below can be made by conventional methods known in the art. Formulation A is for a roll-on; B is for an aerosol; and C is for a pump-spray.

Quantities are expressed as percentages by weight.

TABLE 1

|  | A | B | C |
|---|---|---|---|
| Ethanol | 60.0 | 51.93 | 60.0 |
| Water | 37.9 | 5.5 | 38.15 |
| Klucel 99M[1] | 0.25 | — | — |
| CAP propellant | — | 40.0 | — |
| Isopropyl myristate | — | 1.0 | — |
| Perfume | 1.5 | 1.5 | 1.5 |
| Cosmocil CQ (20% PHMB) | 0.25 | 0.05 | 0.25 |
| Chlorhexidine digluconate | 0.1 | 0.02 | 0.1 |

Klucel 99M (trademark) is hydroxypropyl cellulose from Aqualon.
[1]Hydroxypropylcellulose, ex Aqualon.

[1]Hydroxypropylcellulose, ex Aqualon.

Klucel 99M (trademark) is hydroxypropyl cellulose from Aqualon.

EXAMPLE 2 AND 3

In these Examples, the efficacy of combinations of deodorants was measured by the Deodorant Value Test, a panel test, described below.

The Deodorant Value Test

In this test the deodorant value of a deodorant composition is measured by assessing its effectiveness when applied directly to the skin. The composition is applied to the axillae (armpits) of a panel of human subjects, and its effect at reducing malodour is subsequently assessed.

The test uses a team of 3 or 4 experienced female under-arm odour assessors. These are selected on the basis that they are able to rank correctly the odour intensities of a series of isovaleric acid solutions listed below. The intensities of this series of solutions forms the basis of the 0–5 category scale used to quantify under-arm odour subjectively in the test.

Malodour Category Scale

| SCORE | ODOUR LEVEL | AQUEOUS ISOVALERIC ACID CONC, ml/liter |
|---|---|---|
| 0 | no odour | 0 |
| 1 | slight | 0.013 |
| 2 | definite | 0.053 |
| 3 | moderate | 0.220 |
| 4 | strong | 0.870 |
| 5 | very strong | 3.57 |

New assessors are trained by participation alongside experienced assessors in the tests of deodorancy of under-arm products. Training is complete when the new assessor is able to quantify underarm odour in the present protocol on the same basis as experienced assessors. Discrimination between underarm odour and residual product perfume in the total axillary odour is a key part of the skill of an expert odour assessor.

The panel consists of up to 50 subjects who have been selected by the expert odour assessors on the basis that their body odour is not unusually weak or strong, or uneven between axillae. The panellists are denied the use of any underarm products, and are provided with a non-deodorant soap bar for home use.

The test is run over a five day period, and includes 4 product application-odour assessment cycles. The period between product application to subjects and the assessment of under-arm odour is 5 hours and 24 hours. Only panellists who have not participated in any testing of under-arm products for at least a week previously can take part in this test, because product carry-over effects can occur.

On the first day of the test, the panellist's axillae are washed by the assessors using unperfumed soap. A standard technique is used in which a wet flannel is soaped for 15 seconds, the axilla washed with the flannel for 30 seconds, then wiped with a water-rinsed flannel and dried with a paper towel. A separate flannel is used for each axilla of each panellist. Each panellist wears a different product in each axilla and this is kept constant throughout the test.

A standard product application technique is used; for aerosols, a timed 2 second spray, 6 inches from the axilla is used; for pump sprays, a constant number of pumps is used. For roll-ons and sticks, product can either be applied as a fixed number of strokes or a known weight of product may be applied using a balance to measure the loss in weight of the product.

After 5 hours and 24 hours wear of the test product the odour intensity of each axilla is evaluated by each assessor. Each in turn assigns a score on the scale of 0 to 5, corresponding to the strength of the under-arm malodour.

After a 5 hour assessment panellists go about their normal business for the rest of the day. After 24 hours of the test, panellists are first evaluated for under-arm odour; then they are washed and the products re-applied. The protocol is repeated over 4 consecutive days. On the last day of the test panellists are assessed but no washing is carried out and no further product is applied.

Malodour scores for 5 and 24 hour wear periods are treated separately. Scores from the 4 day's assessments for all expert odour assessors are averaged to give a result for each test product for the week, and these are then averaged to give a team score. The results are analysed using a SAS-based Analysis of Variance routine which takes into account the factors which lead to variability, e.g. subject, day, left/right bias. The analysis also gives the difference in malodour score needed for a result to be statistically significant at the p=0.05 level. The Deodorant Value accorded to a test composition is the difference in score between the test composition and a placebo. This test for determining the Deodorant Value of a deodorant composition for use in accordance with the invention is generally based on the test devised by Whitehouse and Carter as published in 'The Proceedings of the Scientific Section of the Toilet Goods Association", No. 48, December 1967 at pages 31–37 under the title "Evaluation of Deodorant Toilet Bars".

The test described in that publication has however generally been modified in three main ways: firstly, the product is applied directly to the axillae rather than by way of a soap bar wash, secondly, a 0 to 5 instead of a 0 to 10 grading scale was employed and, thirdly, grading of odour intensity was performed 5 hours and 24 hours instead of just 24 hours after treatment. This test is referred to herein as the Deodorant Value Test.

In Example 2, a comparison was made between the deodorant efficacy of ethanolic solutions of respectively D—chlorhexidine digluconate, (CHDG); E—Cosmocil CQ; and F—a mixture of half the concentration of each. The solutions were thickened with 0.25% w/w Klucel 99M (hydroxypropyl-cellulose). The compositions were applied using a roll-on. The results for Example 2 are summarised in Table 2 below.

TABLE 2

| | Deodorant active | Mean Malodour Score after 24 hours |
|---|---|---|
| D | 0.204% CHDG | 2.04 |
| E | 0.50% Cosmocil CQ (20% active) | 1.88 |
| F | 0.102% CHDG + 0.25% Cosmocil CQ (20% active) | 1.58 |
| | Significant Difference (95%) | 0.15 |

From Table 2, it can be seen that the combination according to invention F, i.e. the combination of CHDG and PHMB in ethanol was more efficacious to a statistically significant extent than either the comparative compositions D and E, namely CHDG or PHMB in ethanol.

In Example 3, non-thickened alcoholic aerosol formulations were prepared containing the concentrations of CHDG and PHMB shown in Table 3 below.

TABLE 3

| | Deodorant active | Mean Malodour Score after 24 hours |
|---|---|---|
| G | 0.04% CHDG | 1.73 |
| H | 0.10% Cosmocil CQ (20% active) | 1.88 |
| I | 0.02% CHDG + 0.05% Cosmocil CQ (20% active) | 1.52 |
| | Significant Difference (95%) | 0.15 |

From Table 3, it can be seen that the combination according to invention I, i.e. the combination of CHDG and PHMB in ethanol was more efficacious to a statistically significant extent than either the comparative compositions G and H, namely CHDG or PHMB in ethanol.

We claim:

1. A deodorant composition for topical application to human skin comprising in combination an effective amount of polyhexamethylene biguanide and an effective amount of chlorhexidine in a cosmetically acceptable carrier.

2. A deodorant composition according to claim 1 comprising polyhexamethylene biguanide in the form of a cosmetically acceptable salt.

3. A deodorant composition according to claim 1 comprising chlorhexidine in the form of a cosmetically acceptable salt.

4. A deodorant composition according to claim 1 comprising polyhexamethylene biguanide as 0.001 to 1.0% by weight of the composition.

5. A deodorant composition according to claim 1 comprising chlorhexidine as 0.005 to 0.5% by weight of the composition.

6. A deodorant composition according to claim 1 comprising chlorhexidine and polyhexamethylene biguanide in a weight ratio of from 1:1 to 4:1.

7. A deodorant composition according to claim 1 comprising a monohydric C1 to C4 alcohol.

8. A deodorant composition according to claim 7 comprising ethanol present in weight ratio to the combined weight of chlorhexidine and polyhexamethylene biguanide in the range of from 100:1 to 4000:1.

9. Cosmetic method of preventing or reducing malodour by topically applying to human skin a deodorising composition according to claim 1.

10. A deodorant composition according to claim 7, wherein the monohydric C1 to C4 alcohol is ethanol.

* * * * *